United States Patent [19]
Turturro et al.

[11] Patent Number: 5,746,216
[45] Date of Patent: May 5, 1998

[54] ENDOSCOPIC MULTIPLE SAMPLE BIOPTOME WITH ENHANCED BITING ACTION

[75] Inventors: Vincent Turturro, Miramar; Matthew A. Palmer, Miami; Charles R. Slater, Fort Lauderdale; Saul Gottlieb, Miami, all of Fla.

[73] Assignee: Symbiosis Corporation, Miami, Fla.

[21] Appl. No.: 771,576

[22] Filed: Dec. 20, 1996

Related U.S. Application Data

[60] Division of Ser. No. 412,058, Mar. 28, 1995, Pat. No. 5,636,639, which is a continuation-in-part of Ser. No. 189,937, Feb. 1, 1994, Pat. No. 5,542,432.

[51] Int. Cl.⁶ ................................... A61B 10/00
[52] U.S. Cl. ................................... 128/751
[58] Field of Search ................... 128/749, 751, 128/753; 606/205–208, 167; 600/104, 105

[56] References Cited

U.S. PATENT DOCUMENTS

| | | |
|---|---|---|
| 4,427,014 | 1/1984 | Bel et al. ................... 128/751 |
| 5,052,402 | 10/1991 | Bencini et al. ................... 128/751 |
| 5,318,589 | 6/1994 | Litchman ................... 128/751 X |

Primary Examiner—Jennifer Bahr
Assistant Examiner—Samuel Gilbert
Attorney, Agent, or Firm—David P. Gordon

[57] ABSTRACT

An endoscopic multiple sample bioptome includes a hollow outer member and an axially displaceable inner member extending therethrough. The proximal ends of the outer and inner members are coupled to an actuator for axially displacing one relative to the other. The distal end of the outer member is coupled to one of a cylinder having a sharp distal edge and a jaw assembly, while the distal end of the inner member is coupled to the other. The jaw assembly includes a pair of opposed, preferably toothed jaw cups each of which is coupled by a resilient arm to a base member. The arms are bent to lie in planes which intersect the axis of the base member and to locate the jaws apart from each other. The base member is mounted inside the cylinder and axial movement of the jaw assembly and cylinder relative to each other draws the arms into the cylinder and brings the jaw cups together in a biting action. The biting action is enhanced according to the invention by arranging the cutting edge of each jaw to lie in a plane which intersects the plane in which the distal portion of the jaw arm lies. The biting action is further enhanced by providing a closing cam on the outer surface of the jaws which is engaged by the cylinder when the jaws are closed. The arrangement of the cutting edges also presents a smooth surface to the interior of an endoscope and the closing cams prevent the sleeve from sliding completely over and off of the jaws.

9 Claims, 3 Drawing Sheets

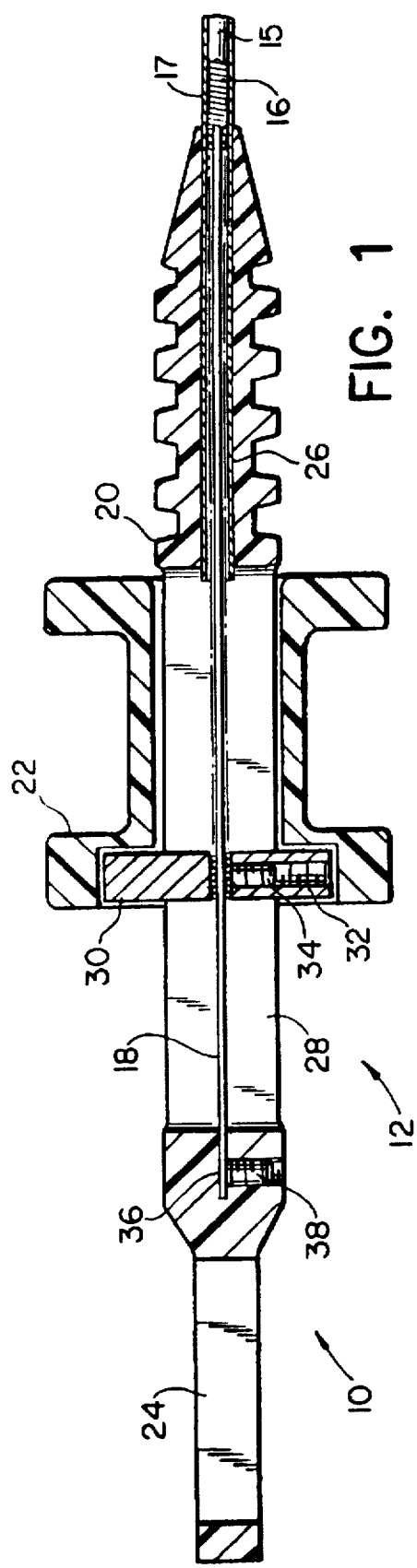
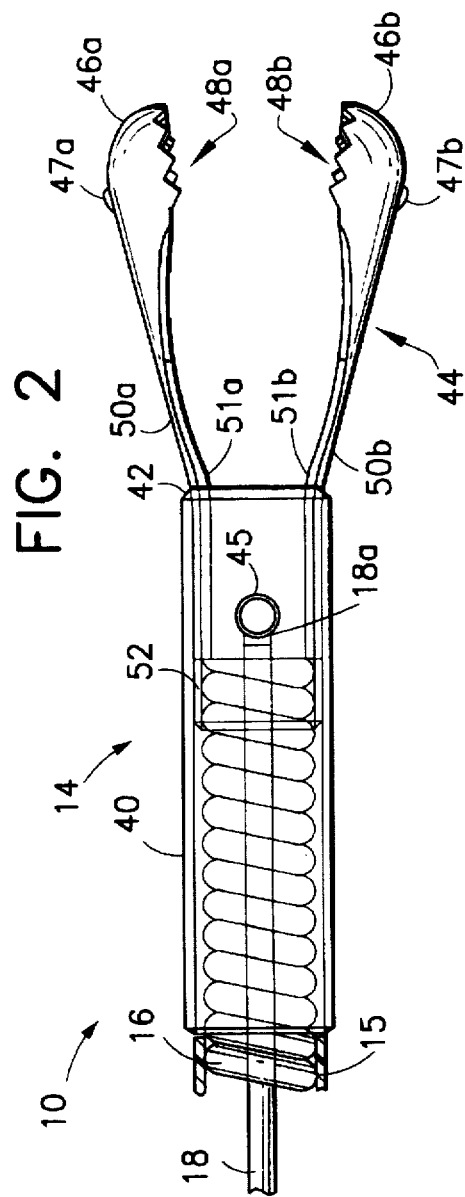

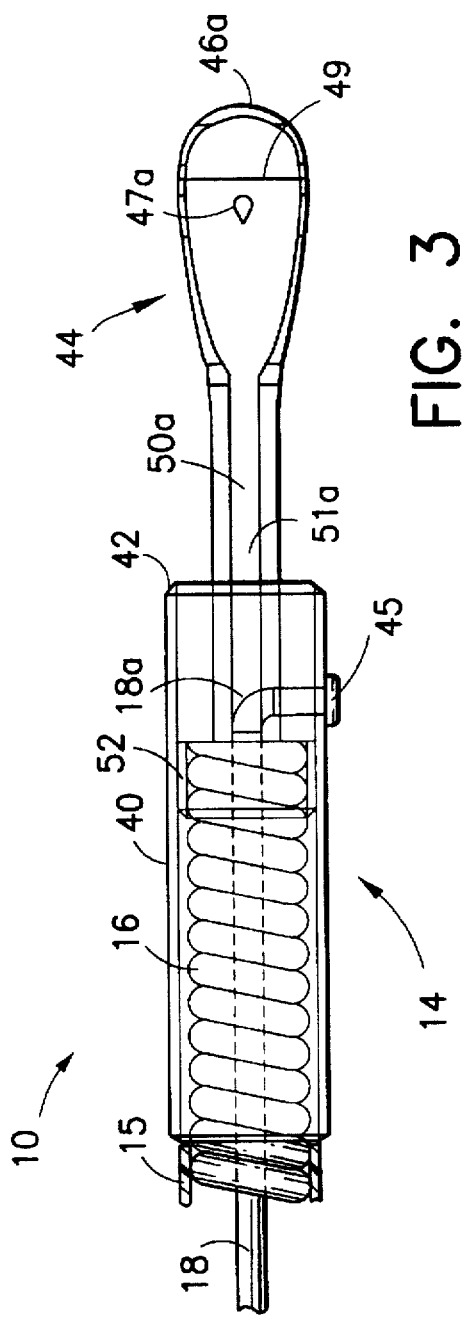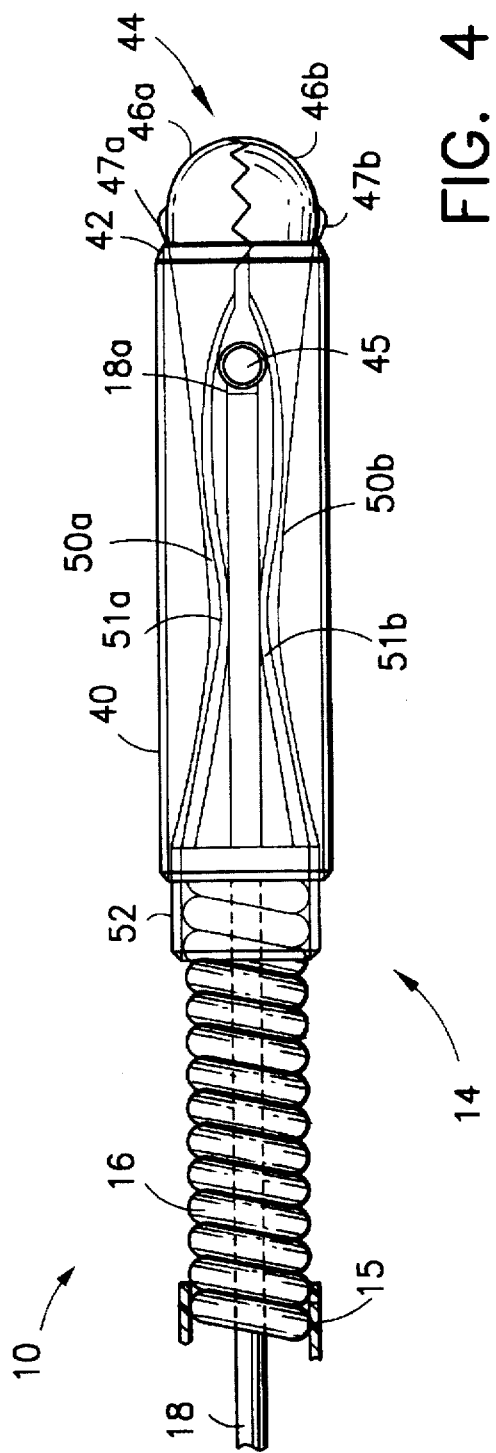

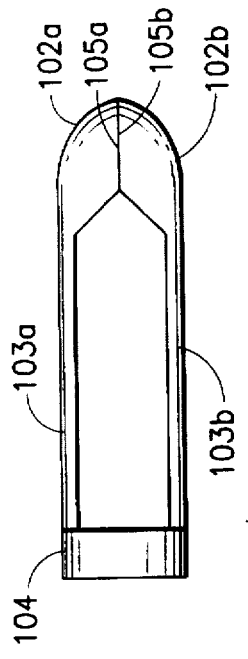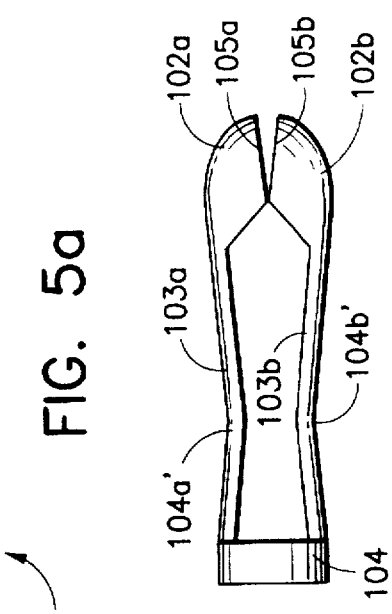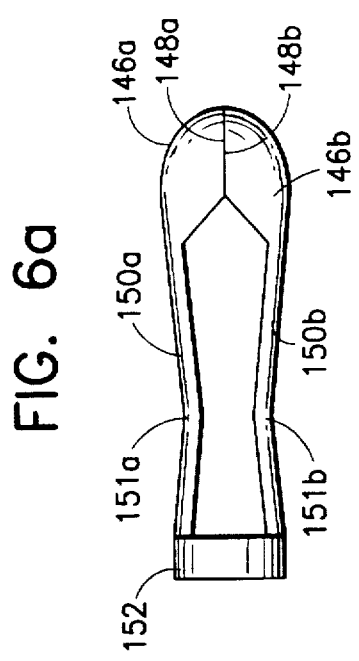
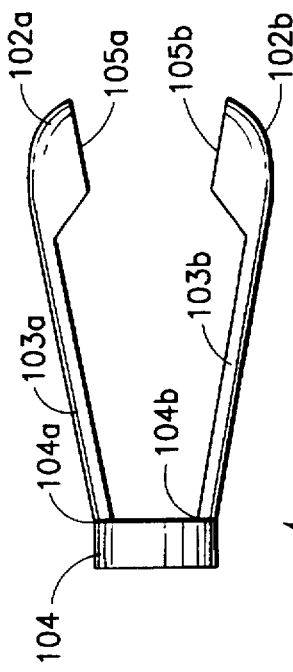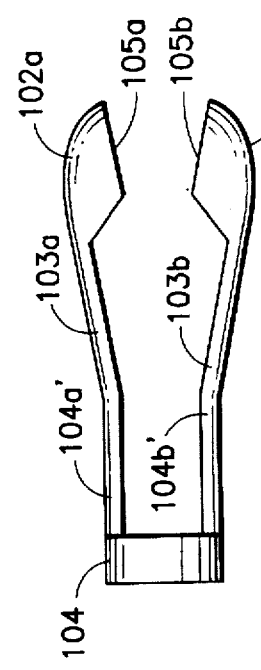
FIG. 5a    FIG. 6a    FIG. 7a
FIG. 5    FIG. 6    FIG. 7

ENDOSCOPIC MULTIPLE SAMPLE BIOPTOME WITH ENHANCED BITING ACTION

This application is a divisional of application Ser. No. 08/412,058, filed on Mar. 28, 1995 Now U.S. Pat. No. 5,636,639, which is a continuation-in-part of application Ser. No. 08/189,937 filed Feb. 1, 1994, and now issue as U.S. Pat. No. 5,542,822 which are hereby incorporated by reference herein in their entireties.

BACKGROUND OF THE INVENTION

1. Field of the Invention

This invention relates to endoscopic surgical instruments. More particularly, this invention relates to an instrument for taking multiple biopsy tissue samples.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. The single-sample limitation of most bioptomes is due to the limited space between the biopsy forceps jaws. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pat. No. 3,989,033 to Halpern et al. and U.S. Pat. No. 4,522,206 to Whipple et al. Both of these devices have a hollow tube with a punch at the distal end and a vacuum source coupled to the proximal end. A tissue sample is cut with the punch and suctioned away from the biopsy site through the hollow tube. It is generally recognized, however, that suctioning tissue samples through a long narrow flexible bioptome is virtually impossible.

Efforts have been made to provide a multiple sampling ability to an instrument which must traverse the narrow lumen of an endoscope. These efforts have concentrated on providing a cylindrical storage space at the distal end of the instrument wherein several tissue samples can be accumulated before the instrument is withdrawn from the endoscope. U.S. Pat. No. 4,651,753 to Lifton, for example, discloses a rigid cylindrical member attached to the distal end of a first flexible tube. The cylindrical member has a lateral opening and a concentric cylindrical knife blade is slidably mounted within the cylindrical member. A second flexible tube, concentric to the first tube is coupled to the knife blade for moving the knife blade relative to the lateral opening in the cylindrical member. A third flexible tube having a plunger tip is mounted within the second flexible tube and a vacuum source (a syringe) is coupled to the proximal end of the third tube. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. The third flexible tube is then pushed forward moving its plunger end against the tissue sample and pushing it forward into a cylindrical storage space at the distal end of the cylindrical member. Approximately six samples can be stored in the cylindrical member, after which the instrument is withdrawn from the endoscope. A distal plug on the cylindrical member is removed and the six samples are collected by pushing the third tube so that its plunger end ejects the samples.

The device of the Lifton patent suffers from several recognizable drawbacks. First, it is often difficult to obtain a tissue sample laterally of the device. Second, in order to expedite the obtaining of a lateral sample, a syringe is used to help draw the tissue into the lateral opening. However, this causes what was once a two-step procedure (position and cut), to become a three-step procedure (position, suction, cut). In addition, the use of a syringe requires an additional hand. Third, the Lifton patent adds a fourth step to the biopsy procedure by requiring that the tissue sample be pushed into the storage space. Thus, in all, the Lifton patent requires substantial effort on the part of the surgeon and an assistant and much of this effort is involved in pushing tubes, an action which is counter-intuitive to classical biopsy sampling. The preferred mode of operation of virtually all endoscopic tools is that a gripping action at the distal end of the instrument is effected by a similar action at the proximal end of the instrument. Classical biopsy forceps jaws are closed by squeezing a manual actuation member in a syringe-like manner.

A more convenient endoscopic multiple sample biopsy device is disclosed in U.S. Pat. N0. 5,171,255 to Rydell. Rydell provides a flexible endoscopic instrument with a knife-sharp cutting cylinder at its distal end. A coaxial anvil is coupled to a pull wire and is actuated in the same manner as conventional biopsy forceps. When the anvil is drawn into the cylinder, tissue located between the anvil and the cylinder is cut and pushed into a storage space within the cylinder. Several samples may be taken and held in the storage space before the device is withdrawn from the endoscope. While the device of Rydell is effective in providing a multiple sample tool where each sample is obtained with a traditional two-step procedure (position and cut), it is still limited to lateral cutting which is often problematic. Traditional biopsy forceps provide jaws which can grasp tissue frontally or laterally. Even as such, it is difficult to position the jaws about the tissue to be sampled. Lateral sampling is even more difficult.

Parent application Ser. No. 08/189,937 discloses an endoscopic multiple sample bioptome having a hollow outer member and an axially displaceable inner member extending therethrough. The proximal ends of the outer and inner members are coupled to an actuator for axially displacing one relative to the other. The distal end of the outer member is coupled to one of a cylinder having a sharp distal edge and a jaw assembly, while the distal end of the inner member is coupled to the other. The jaw assembly includes a pair of opposed, preferably toothed, jaw cups each of which is coupled by a resilient arm to a base member. The resilient arms are bent to urge the jaws away from each other. The base member is mounted inside the cylinder and axial movement of the jaw assembly and cylinder relative to each other draws the resilient arms into the cylinder and brings the jaw cups together in a biting action. Depending on the geometry of the resilient arms, however, when the cylinder is moved over the arms, they may tend to bow inward and prevent a complete closing of the jaws. This results in a less than optimal biting action.

SUMMARY OF THE INVENTION

It is therefore an object of the invention to provide an endoscopic multiple sample bioptome which is not limited to lateral tissue sampling.

It is also an object of the invention to provide an endoscopic multiple sample bioptome which is easy to operate.

It is another object of the invention to provide an endoscopic multiple sample bioptome which is inexpensive to manufacture.

It is still another object of the invention to provide an This invention relates to endoscopic surgical instruments. endoscopic multiple sample bioptome which has all of the advantages of traditional biopsy forceps with the added ability to collect multiple samples.

It is yet another object of the invention to provide an endoscopic bioptome with jaws which completely close.

It is still another object of the invention to provide an endoscopic bioptome which has an enhanced biting action.

In accord with these objects which will be discussed in detail below, the endoscopic bioptome of the present invention includes a relatively long flexible member having a lumen with an axially displaceable wire extending therethrough. The proximal ends of the flexible member and wire are coupled to a manual actuation means for axially displacing one of the flexible member and wire relative to the other. The distal end of the flexible member is coupled to a jaw assembly. The distal end of the wire is coupled to a cylinder which is slidable over the jaw assembly. The jaw assembly includes a pair of opposed jaw cups, each of which is coupled by a narrow arm to a base member and each of which has a sharp cutting edge. The narrow arm of each jaw is a resilient member which includes a portion which is bent away from the longitudinal axis of the cylinder in order to locate the jaw cups substantially apart from each other. The base member of the jaw assembly is mounted inside the cylinder and axial movement of one of the jaw assembly and cylinder relative to the other draws the arms of the jaws into the cylinder or moves the cylinder over the arms of the jaws to bring the jaw cups together in a biting action. In order to assure that the jaws completely close together in a biting action, the jaw cups are provided with a closing cam. The closing cam is preferably a ramped surface on the outer surface of the jaw cup which is engaged by the cylinder to move the jaw cup further closed. In addition to encouraging a complete closing of the jaw cups, the closing cams also prevent the cylinder from moving too far distally over the jaw cups. To further encourage a complete closing, each jaw cups is preferably provided with a cutting edge which lies in a plane which intersects the plane in which the bent portion of the jaw arm lies. In addition to encouraging a complete closing of the jaw cups, the arrangement of the cutting edge in this way provides a smoother outer surface of the closed jaws which is well tolerated by the interior of an endoscope.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation view in partial section of the proximal end of a first embodiment of the invention;

FIG. 2 an enlarged partially transparent side elevation view of the distal end of a first embodiment of the invention with the jaws open;

FIG. 3 is an enlarged transparent top view of the distal end of an embodiment of the invention;

FIG. 4 is a view similar to FIG. 2, but with the jaws closed;

FIG. 5 a schematic view of a first jaw assembly in the open position;

FIG. 5a is a schematic view of the jaw assembly of FIG. 5 in the closed position;

FIG. 6 schematic view of a second jaw assembly in the open position;

FIG. 6a is schematic view of the jaw assembly of FIG. 6 in the close position;

FIG. 7 schematic view of a second embodiment of a jaw assembly according to the invention in the open position; and FIG. 7a is a schematic view of the jaw assembly of FIG. 7 in the closed position.

DETAILED DESCRIPTION OF THE PREFERRED EMBODIMENTS

Referring now to FIGS. 1 through 4, a first embodiment of the multiple sample bioptome 10 includes a proximal handle 12 and a distal end effector 14. A long flexible coil 16 having an axially displaceable control wire 18 extending therethrough couples the handle 12 and the end effector 14. The coil 16 is preferably covered with a PTFE, FEP or polyolefin sheath 15 along substantially all of its length and a strain relief sleeve 17 covering a portion of the coil which extends from the handle 12. The control wire 18 is preferably flexible but longitudinally inelastic and is ideally formed from 304 Steel and provided with and outer diameter of approximately 0.018 inch. The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a central through hole 32 and a radially engaging set screw 34. According to the first embodiment of the invention, a short bore 36 and a radially engaging set screw 38 are provided in the shaft 20 distal of the thumb ring 24 with the bore 36 communicating with the longitudinal slot 28. In the first embodiment of the invention, the proximal end of the coil 16 extends into the central through hole 32 in the cross member 30 and is fixed there by the set screw 34. The proximal end of the control wire 18, passes through slot 28, is inserted into the short bore 36, and held there by the set screw 38. From the foregoing, those skilled in the art will appreciate that relative movement of the shaft 20 and spool 22 results in movement of the control wire 18 relative to the coil 16. Such action results in actuation of the end effector 14 as described in detail below.

Turning now to FIGS. 2 through 4, the end effector 14 includes a cylindrical sleeve 40 (preferably having a knife-sharp distal edge 42) and a jaw assembly 44. The jaw assembly 44 includes a pair of opposed jaw cups 46a, 46b each preferably having a plurality of sharp, radially arranged teeth 48a, 48b. A resilient, preferably narrow, arm 50a, 50b extends proximally from each jaw cup 46a, 46b. A cylindrical base member 52 joins the proximal ends of the arms 50a, 50b. As seen best in FIG. 2, the narrow resilient arms 50a, 50b are bent apart from each other at a point 51a, 51b between the cylindrical base member 52 and the respective jaw cups 46a, 46b, thereby locating the jaw cups 46a, 46b apart from each other and placing the distal portion of each arm in a plane which intersects the axis of the base member. The cylindrical base member 52 is coupled to the distal end of the flexible coil 16 by welding, soldering, crimping, or any other suitable manner. The cylindrical sleeve 40 is coupled to the distal end of the control wire 18 by providing the sleeve 40 with a lateral hole 45 which engages a bent end 18a of the control wire 18. As shown in FIGS. 2 through 4, the bent end 18a of the control wire 18 is welded to the hole 45 in the side of the sleeve 40. However, as described in detail in the parent application, other methods of coupling the control wire to the sleeve are possible. The cylindrical sleeve 40 is slidably mounted over the cylindrical base member 52 as shown in FIGS. 2 and 3 and is axially movable over the resilient arms 50a, 50b as shown in FIG. 4.

According to the invention, the jaw cups 46a, 46b are preferably each provided with a closing cam 47a, 47b on their outer surface. Each closing cam is preferably an inclined bump which rises from the surface of the jaw cup in the distal direction. In addition, the teeth 48a, 48b (i.e., the top points or valleys) on each jaw cup are preferably arranged in a plane which is angled relative to the plane of the bent portion of the arm so that the respective teeth fully engage each other when the jaws are closed as shown in FIG. 4 and discussed below in more detail with reference to FIGS. 5-7.

As seen in FIG. 3, the jaw cups 46a, 46b have an eccentric cross section with their widest point indicated by the line 49. Distal of the line 49 the jaw cups are substantially hemispherical, and proximal of the line 49 the jaw cups are substantially hemi-elliptical. The closing cams or ramps 47a, 47b are preferably located proximal of the widest portions of the jaws, i.e., proximal of the line 49. It will also be seen that the side walls of the jaw cups 46a, 46b taper towards the arms 50a, 50b to provide a smooth transition from the jaw cups to the arms.

From the foregoing description and with reference to FIGS. 1 through 4, those skilled in the art will appreciate that when the spool 22 and the shaft 20 are axially displaced relative to each other, the cylindrical sleeve 40 and the jaw assembly 44 are similarly axially displaced relative to each other, from the positions shown in FIG. 2 to the positions shown in FIG. 4 and vice versa. It will also be appreciated that when the spool 22 and shaft 20 are in the approximate position shown in FIG. 1, the cylindrical sleeve 40 and the jaw assembly 44 will be in the approximate position shown in FIG. 2; i.e., with the jaws open. Thus, those skilled in the art will further appreciate that when the spool 22 is moved towards the thumb ring 24, or vice versa, the cylindrical sleeve 40 and the jaw assembly 44 will be brought into the approximate position shown in FIG. 4; i.e., with the jaws closed. Moreover, it will also be appreciated that it is preferable to move the thumb ring 24 relative to the spool 22, rather than vice versa since that will move the cylindrical sleeve 40 relative to the jaw assembly 44 rather than vice versa. This is desirable so that the jaw assembly is not moved away from a tissue sample while the jaws are being closed. In either case, as the arms 50a, 50b are drawn together by the cylindrical sleeve 40, the arms tend to flex at their coupling to the cylindrical base member 52, as seen in FIG. 4, rather than at their respective bends 51a, 51b. This geometry of the arms is compensated for by a special arrangement of the teeth of the jaws which will be understood from the following discussion.

Referring now to FIGS. 5 and 5a, a jaw assembly 101 which includes a first jaw cup 102a and a second jaw cup 102b. Each of the jaw cups 102a, 102b are coupled by a respective resilient arm 103a, 103b to a cylindrical base member 104. The arms 103a, 103b are bent away from each other (away from the longitudinal axis of the base member) at the points 104a, 104b where they meet the base member 104. The jaw cups 102a, 102b are each provided with a cutting edge 105a, 105b, which may include an array of teeth or which may simply be a sharp edge. When the sleeve (not shown) is moved over the jaw assembly, the arms 103a, 103b are flexed at the points 104a, 104b and the jaws 102a, 102b are brought together as shown in FIG. 5a so that their cutting edges engage each other. Those skilled in the art will appreciate that in this arrangement, the arms 103a, 103b are moved into a position where they are substantially parallel when the jaws are closed. Therefore, the cutting edge of each jaw should be arranged so that it lies in a plane which is substantially parallel to the arm of the jaw.

Referring back to FIGS. 2-4, it will be appreciated that, due to the geometry of the end effector 14 and its coupling with the coil 16 and the pull wire 18, it is difficult to provide the necessary bends 51a, 51b in the jaw arms 50a, 50b at the point where they meet the base member 52. This is because a certain amount of space is required between the base member and the arm bends to accommodate the coupling (18a, 45) of the pull wire 18 with the cylindrical sleeve 40.

Turning now to FIGS. 6 and 6a, the same jaw assembly 101 as described above, is provided with bends 104'a and 104'b in its arms 103a, 103b at points distal of the cylindrical base member 104. Despite the location of these bends, the resiliency of the arms will cause them to flex at their connection to the base member 104 when the sleeve (not shown) is moved over the jaw assembly. When the arms 103a, 103b flex as shown in FIG. 6a, the jaw cups 102a, 102b are brought together, but their cutting edges 105a, 105b do not completely engage. This is because the cutting edges 105a, 105b are arranged to lie in a plane which is substantially parallel to distal portion of the arms 103a, 103b, and the arms 103a, 103b are never brought into parallel alignment, due to the bends 104'a, 104'b. The failure of the cutting edges to fully engage results in two disadvantages: an incomplete cutting action, and exposed sharp edges which can damage the interior of an endoscope. Therefore, in order to provide for the complete engagement of the cutting edges of the jaws, the geometry of the cutting edges must be altered.

FIGS. 7 and 7a show a jaw assembly 144 according to the invention. The jaw assembly 144 includes a first jaw cup 146a and a second jaw cup 146b. Each of the jaw cups are coupled by a respective resilient arm 150a, 150b to a cylindrical base member 152. The arms are bent away from each other (and away from the longitudinal axis of the base member) at points 151a, 151b which are distal of the base member 152. The jaw cups 146a, 146b are each provided with a cutting edge 148a, 148b which is arranged to lie in a plane which is not parallel to the distal (bent away) portion of the respective arm 150a, 150b In particular, each of the cutting edges is arranged to lie in a plane which intersects the plane in which the distal portion of the jaw arm lies. When the sleeve (not shown) is moved over the jaw assembly, the arms 150a, 150b flex at their connection to the base member 152 and the jaws 146a, 146b are brought together as shown in FIG. 7a so that their cutting edges 148a, 148b substantially completely engage each other.

Referring once again to FIGS. 2 and 4, it will be appreciated that the jaw assembly 44 is provided with cutting teeth 48a, 48b arranged in a plane as just described to achieve a substantially complete intermeshing of the teeth when the jaws are closed. It will further be appreciated that the closing cams 47a, 47b further encourage a complete meshing of jaw teeth particularly in the distal portion of the jaws. The closing cams further prevent the sleeve 40 from moving too far distally over the jaw cups. This is an important safety advantage in case the sleeve 40 should become disengaged from the pull wire 18, as the closing cams will prevent the sleeve from falling off the bioptome and becoming lost inside the body of the patient.

Those skilled in the art will appreciate that the bioptome according to the present invention is used in substantially the same way as explained in the parent application which was previously incorporated herein by reference. The instant bioptome, however, has an enhanced biting action. Like the bioptome of the parent application, the jaw assembly may be coupled to the pull wire and the cylindrical sleeve coupled to the coil, rather than vice versa, and the couplings may be effected in several different ways. Several different types of actuating means (e.g., scissors grip) may be used other than the spool and thumb ring arrangement shown herein. The jaws may be manufactured by several methods including stamping, laser cutting, etc. In the presently preferred embodiment, the jaws are formed as flat blanks from a sheet of 410 stainless steel using a die and punch. The formed blanks are placed in a die having a concave surface corresponding to the outer surface of the jaw cups and an indentation in the concave surface corresponding to the closing cam. A punch having a convex surface corresponding to the interior surface of the jaw cups and a raised bump corresponding to an interior of the closing cam is pressed onto the flat blank and the jaw cup is cold formed from the flat blank.

There have been described and illustrated herein several embodiments of an endoscopic multiple sample bioptome. While particular embodiments of the invention have been described, it is not intended that the invention be limited thereto, as it is intended that the invention be as broad in scope as the art will allow and that the specification be read likewise. Thus, while particular configurations of the cutting edges of the jaws, it will be appreciated that other types of cutting edges could be utilized. In particular, the cutting edges may have teeth or a toothless sharp edge, or a combination of both. The teeth may be radially arranged or arranged in another manner. Also, while the distal end of the cylindrical sleeve has been shown and described as having a knife-sharp edge, a sleeve without a sharp edge could also be used with the inventive jaw assembly. Moreover, while particular configurations have been disclosed in reference to the closing cams, it will be appreciated that other configurations could be used as well. For example, rather than have closing cams ramping outwardly from the surface of the jaws, the jaws themselves may be arranged to increase in diameter such that the outer diameter of the closed jaw cups where the cam would otherwise be located is larger than the inner diameter of the cylinder. In other words, the jaw cups may be arranged to take on a bulbous form in order to expedite closing of the cups by the cylinder and prevent the cylinder from passing over the jaws. Furthermore, it will be appreciated that while the invention was described as advantageously permitting the obtaining of multiple biopsies without removal from the surgical site, the apparatus of the invention, if desired, could still be used for obtaining single biopsies at a time. It will therefore be appreciated by those skilled in the art that yet other modifications could be made to the provided invention without deviating from its spirit and scope as so claimed.

We claim:

1. An endoscopic bioptome, comprising:
   a) a hollow outer member having a proximal and a distal end;
   b) an inner control member having a proximal and a distal end and extending through said hollow outer member;
   c) a cylinder having a longitudinal axis, said cylinder being coupled to said distal end of one of said hollow outer member and said inner control member;
   d) a jaw assembly including a base member and a pair of resilient arms extending distally from said base member, each of said resilient arms terminating in a jaw cup having a cutting edge, each of said resilient arms having a portion bent away from said longitudinal axis of said cylinder, said base member being coupled to said distal end of the other of said hollow outer member and said inner control member; and
   e) actuation means coupled to said proximal end of said hollow outer member and to said proximal end of said inner control member for axially displacing one of said hollow outer member and said inner control member relative to the other of said hollow outer member and said inner control member, whereby said cylinder extends around said pair of resilient arms and closes said jaw cups, wherein,
      at least one of said jaw cups has an outer surface which includes a ramp which is engaged by said cylinder when said jaw cups are closed.

2. An endoscopic bioptome according to claim 1, wherein:
   said ramp is a closing cam,
   both of said jaw cups are provided with closing cams on said outer surfaces of said jaw cups, and
   each of said jaw cups has an inner surface defining said cutting edge.

3. An endoscopic bioptome according to claim 1, wherein:
   each of said jaw cups has a cutting edge which lies in a plane which intersects a plane in which said portion of the resilient arm which is bent away from said longitudinal axis of said cylinder lies.

4. An endoscopic bioptome according to claim 1, wherein:
   said cylinder has a sharp distal edge.

5. An endoscopic bioptome according to claim 1, wherein:
   each of said resilient arm portions is bent away from said longitudinal axis of said cylinder at a point distal of said base member, and a proximal portion of each of said resilient arms lies in a plane that is substantially parallel to said longitudinal axis of said cylinder.

6. A jaw assembly for use in an endoscopic bioptome, comprising:

a) a base member having a longitudinal axis; and
b) a pair of resilient arms extending distally from said base member, each of said resilient arms terminating in a jaw cup having a cutting edge, each of said resilient arms having a portion being bent away from said longitudinal axis of said base member and lying in a plane which intersects said longitudinal axis of said base member, wherein,
at least one of said jaw cups is provided with a closing cam.

7. A jaw assembly according to claim 6, wherein:
both of said jaw cups have a closing cam, and each of said jaw cups has an outer surface and an inner surface defining said cutting edge and said closing cam is an inclined ramp on said outer surface.

8. A jaw assembly according to claim 6, wherein:
each of said jaw cups has a cutting edge which lies in a plane which intersects a plane in which said bent away portion of said resilient arm lies.

9. A jaw assembly according to claim 6, wherein:
each of said resilient arm portions is bent away from said longitudinal axis of said base member at a point distal of said base member, and a proximal portion of each of said resilient arms lies in a plane which is substantially parallel to said longitudinal axis of said base member.

* * * * *